(12) United States Patent
Suh et al.

(10) Patent No.: US 11,447,435 B2
(45) Date of Patent: Sep. 20, 2022

(54) METHOD FOR PRODUCING BUTADIENE

(71) Applicant: LG CHEM, LTD., Seoul (KR)

(72) Inventors: Myungji Suh, Daejeon (KR); Jun Han Kang, Daejeon (KR); Kyong Yong Cha, Daejeon (KR); Dong Hyun Ko, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 17/050,031

(22) PCT Filed: Jul. 10, 2019

(86) PCT No.: PCT/KR2019/008474
§ 371 (c)(1),
(2) Date: Oct. 23, 2020

(87) PCT Pub. No.: WO2020/111431
PCT Pub. Date: Jun. 4, 2020

(65) Prior Publication Data
US 2021/0238111 A1    Aug. 5, 2021

(30) Foreign Application Priority Data
Nov. 30, 2018   (KR) ......................... 10-2018-0152167

(51) Int. Cl.
*C07C 5/48*     (2006.01)
*B01J 23/31*    (2006.01)
(Continued)

(52) U.S. Cl.
CPC ................. *C07C 5/48* (2013.01); *B01J 23/31* (2013.01); *B01J 23/80* (2013.01); *B01J 37/0236* (2013.01);
(Continued)

(58) Field of Classification Search
CPC . C07C 5/48; C07C 2523/31; C07C 2523/745; C07C 2523/80; C07C 11/167;
(Continued)

(56) References Cited

U.S. PATENT DOCUMENTS

2012/0130137 A1    5/2012  Orta et al.
2014/0163290 A1*   6/2014  Grune ................... B01J 23/882
                                                            585/626

(Continued)

FOREIGN PATENT DOCUMENTS

CN      103071544 A    5/2013
EP       3272417 A1    1/2018
(Continued)

*Primary Examiner* — Youngsul Jeong
*Assistant Examiner* — Jason Y Chong
(74) *Attorney, Agent, or Firm* — Dentons US LLP (57) ABSTRACT

An exemplary embodiment of the present application provides a method for preparing butadiene, the method comprising a process of performing an oxidative dehydrogenation reaction by introducing a reactant comprising butene, oxygen, nitrogen, and steam into a reactor which is filled with a catalyst, in which during a first start-up of the oxidative dehydrogenation reaction, the oxygen is introduced into the reactor before the butene, or the oxygen is introduced into the reactor simultaneously with the butene.

11 Claims, 1 Drawing Sheet

(51) Int. Cl.
  B01J 23/80  (2006.01)
  B01J 37/02  (2006.01)
  B01J 37/03  (2006.01)

(52) U.S. Cl.
  CPC ......... B01J 37/038 (2013.01); *C07C 2523/31* (2013.01); *C07C 2523/80* (2013.01)

(58) Field of Classification Search
  CPC . B01J 23/002; B01J 23/31; B01J 23/80; B01J 37/0236; B01J 37/033; B01J 37/038; B01J 21/04; B01J 2219/0004; B01J 2219/00306; B01J 2523/54; B01J 2523/68
  See application file for complete search history.

(56) References Cited

U.S. PATENT DOCUMENTS

| | | |
|---|---|---|
| 2014/0273794 A1 | 9/2014 | Fridman et al. |
| 2015/0126788 A1 | 5/2015 | Takagaki et al. |
| 2016/0289145 A1* | 10/2016 | Lee .................. C07C 7/005 |
| 2016/0347686 A1 | 12/2016 | Grüne et al. |
| 2016/0354764 A1 | 12/2016 | Park et al. |
| 2018/0147561 A1 | 5/2018 | Ungelenk et al. |
| 2019/0134612 A1 | 5/2019 | Hwang et al. |
| 2019/0144362 A1 | 5/2019 | Suh et al. |
| 2019/0337870 A1 | 11/2019 | Ungelenk et al. |
| 2020/0039901 A1 | 2/2020 | Ungelenk et al. |

FOREIGN PATENT DOCUMENTS

| | | |
|---|---|---|
| JP | 2010-280653 A | 12/2010 |
| JP | 2011006395 A | 1/2011 |
| JP | 2017502988 A | 1/2017 |
| JP | 2018517557 A | 7/2018 |
| KR | 10-2013-0046458 A | 5/2013 |
| KR | 10-2014-0121467 A | 10/2014 |
| KR | 10-2015-128896 A | 11/2015 |
| KR | 10-1577759 B1 | 12/2015 |
| KR | 101577759 B1 * | 12/2015 |
| KR | 10-2016-0083224 A | 7/2016 |
| KR | 10-2016-0143272 A | 12/2016 |
| KR | 10-2017-0108277 A | 9/2017 |
| KR | 10-2018-0046648 A | 5/2018 |
| WO | 2014/128718 A2 | 8/2014 |
| WO | 2017122103 A1 | 7/2017 |
| WO | 2017146024 A1 | 8/2017 |
| WO | 2018/029215 A1 | 2/2018 |
| WO | 2018/139776 A1 | 8/2018 |
| WO | 2018/178005 A1 | 10/2018 |

* cited by examiner

METHOD FOR PRODUCING BUTADIENE

The present application is a National Phase entry pursuant to 35 U.S.C § 371 of International Application No. PCT/KR2019/008474 filed on Jul. 10, 2019, and claims priority to and the benefit of Korean Patent Application No. 10-2018-0152167 filed in the Korean Intellectual Property Office on Nov. 30, 2018, the entire contents of which are incorporated herein by reference.

FIELD

The present application relates to a method for preparing butadiene.

BACKGROUND

Butadiene is an intermediate of petroleum chemical product, and demands for butadiene and the value thereof are gradually increasing globally. Butadiene has been prepared by using naphtha cracking, direct dehydrogenation reaction of butene, oxidative dehydrogenation reaction of butene, and the like.

Domestic butadiene production is done almost through a naphtha cracking process. However, since the naphtha cracking process is not a single process for production of only butadiene, the high domestic demand for butadiene may not be satisfied only by butadiene produced from naphtha cracking. Therefore, there is a need for developing a process and a catalyst for the main purpose of producing butadiene (an on-purpose butadiene production process). One of those considered as the butadiene production reaction is a direct dehydrogenation reaction of n-butene, but this reaction is an endothermic reaction, requires high temperature conditions for production of butadiene with a high yield, and thus is not suitable for a commercialization process for producing butadiene.

Therefore, there is a need for developing a technique for producing butadiene using an oxidative dehydrogenation reaction of butene, which is thermodynamically advantageous and requires a low-temperature reaction condition instead of a direct dehydrogenation reaction.

SUMMARY

An exemplary embodiment of the present application provides a method for producing butadiene, the method comprising a process of performing an oxidative dehydrogenation reaction by introducing a reactant comprising butene, oxygen, nitrogen, and steam into a reactor which is filled with a catalyst, in which during a first start-up of the oxidative dehydrogenation reaction, the oxygen is introduced into the reactor before the butene, or the oxygen is introduced into the reactor simultaneously with the butene.

According to an exemplary embodiment of the present application, during a first start-up of an oxidative dehydrogenation reaction, it is possible to prevent activity of a catalyst from deteriorating by introducing oxygen into a reactor before the butene, or introducing oxygen into a reactor simultaneously with the butene.

Further, according to an exemplary embodiment of the present application, by performing a purge process while maintaining the same temperature as the temperature during an oxidative dehydrogenation reaction at the time of an emergency situation in which at least a part of a reactant comprising butene, oxygen, nitrogen, and steam is stopped from being supplied, it is possible to reduce the energy and time cost consumption such as a temperature increasing process of a reactor, and to quickly recover from the emergency situation to a normal operational state.

In addition, according to an exemplary embodiment of the present application, at the time of an emergency situation in which at least a part of a reactant comprising butene, oxygen, nitrogen, and steam is inadvertently stopped from being supplied, the constitution of the reactant which continues to be supplied may be a basis for determining whether the activity of a catalyst deteriorates. Accordingly, it is possible to reduce the energy and time cost consumption by enabling the re-operation or catalyst replacement to be determined.

DETAILED DESCRIPTION

Hereinafter, the present specification will be described in more detail.

In the present specification, the 'yield (%)' is defined as a value obtained by dividing the weight of butadiene as a product of an oxidative dehydrogenation reaction by the weight of butene (BE) as a raw material. For example, the yield may be represented by the following equation.

Yield (%)=[(the number of moles of butadiene produced)/(the number of moles of butene supplied)]×100

In the present specification, the 'conversion (%)' refers to a rate at which a reactant is converted into a product, and for example, the conversion of butene may be defined by the following equation.

Conversion (%)=[(the number of moles of butene reacted)/(the number of moles of butene supplied)]×100

In the present specification, the 'selectivity (%)' is defined as a value obtained by dividing the change amount of butadiene by the change amount of butene. For example, the selectivity may be represented by the following equation.

Selectivity (%) of butadiene=[(the number of moles of butadiene produced)/(the number of moles of butene reacted)]×100

Selectivity (%) of $CO_x$=[(the number of moles of $CO_x$ produced/4)/(the number of moles of butene reacted)]×100

Butadiene is an important base oil that is used as a raw material for various synthetic rubbers. Examples of methods for preparing butadiene roughly comprise naphtha cracking, direct dehydrogenation reaction of normal-butene, oxidative dehydrogenation reaction of normal-butene, and the like. Among them, the oxidative dehydrogenation reaction of normal-butene has attracted attention as a useful on-purpose butadiene production method because the oxidative dehydrogenation reaction is thermodynamically more advantageous and a more efficient process than other processes.

During the oxidative dehydrogenation reaction process, when the reaction process is completed, a catalyst is exposed to an atmosphere different from the operation state of a continuous process that maintained the equilibrium state while stopping the adjustment of the reaction temperature and the supply of the reactant, so that deactivation of the catalyst is likely to occur, and the catalytic activity may be reduced when the reaction process is restarted, and accordingly, a reduction in butadiene yield of the reaction process and a cost consumption for catalyst replacement may occur.

Thus, the present application is intended to provide a method for preparing butadiene, which is capable of preventing deactivation of a catalyst and securing reproducibility of the catalytic activity by establishing an operation method and an operation completion method of a catalyst reactor.

The method for producing butadiene according to an exemplary embodiment of the present application is characterized by comprising a process of performing an oxidative dehydrogenation reaction by introducing a reactant comprising butene, oxygen, nitrogen, and steam into a reactor which is filled with a catalyst, and introducing the oxygen into the reactor before the butene, or introducing the oxygen into the reactor simultaneously with the butene during a first start-up of the oxidative dehydrogenation reaction.

In an exemplary embodiment of the present application, oxygen and nitrogen are simultaneously introduced into a reactor during a first start-up of the oxidative dehydrogenation reaction, then steam may be introduced into the reactor, and then butene may be finally introduced into the reactor. In addition, in another exemplary embodiment of the present application, nitrogen and steam are simultaneously introduced into the reactor during a first start-up of the oxidative dehydrogenation reaction, then oxygen and butene may be simultaneously introduced into the reactor.

In an exemplary embodiment of the present application, the oxidative dehydrogenation reaction may be performed according to the following Reaction Formula 1 or Reaction Formula 2.

$$C_4H_8 + \tfrac{1}{2}O_2 \rightarrow C_4H_6 + H_2O \qquad \text{[Reaction Formula 1]}$$

$$C_4H_{10} + O_2 \rightarrow C_4H_6 + 2H_2O \qquad \text{[Reaction Formula 2]}$$

The oxidative dehydrogenation reaction is a reaction in which oxygen participates in the reaction, and it is known that the catalyst follows a redox mechanism. Here, oxygen contributes to maintaining the activity by suppressing the reduction of the catalyst. Accordingly, the activity is likely to deteriorate when the catalyst is exposed to an oxygen-deficient environment. In particular, when the catalyst is exposed to hydrocarbons such as butene, deterioration in activity of the catalyst may be accelerated. In addition, since oxygen also serves to oxidize and remove by-products, deposition caused by by-products with a high carbon number and a high-boiling point may occur on the catalyst under an oxygen-deficient environment. This may have a serious adverse effect on the catalyst life.

In an exemplary embodiment of the present application, the steam to be introduced into the reactor may be fresh steam or wastewater distillation steam recycled from the product after the oxidative dehydrogenation reaction.

When the steam to be introduced into the reactor is wastewater distillation steam recycled from the product after the oxidative dehydrogenation reaction, it is preferred to introduce the wastewater distillation steam into the reactor simultaneously with oxygen.

The wastewater distillation steam may be used by recovering steam introduced into the reactor by cooling the product after the reaction and steam produced from the reaction as water, and heating the water to recycle the water in the form of steam and introduce the water in the form of steam into the reactor. In the cooling process, some products are condensed together, so that the wastewater distillation steam may comprise up to 1 wt % of hydrocarbons. Accordingly, when wastewater distillation steam is supplied to a catalyst under an oxygen-deficient environment, hydrocarbons which wastewater distillation steam comprises are deposited on the catalyst, and thus are likely to reduce the life of the catalyst.

In an exemplary embodiment of the present application, when at least a part of a reactant comprising butene, oxygen, nitrogen, and the steam is stopped from being supplied, the oxidative dehydrogenation reaction is stopped, a purge process is performed, and the purge process may be performed by introducing one or more of air and steam into a reactor.

In an exemplary embodiment of the present application, a case where at least a part of the reactant comprising butene, oxygen, nitrogen, and the steam is stopped from being supplied may comprise a case where the supply of the reactant is stopped because the operation of the oxidative dehydrogenation reaction process needs to be stopped, a case where at least a part of the reactant comprising butene, oxygen, nitrogen, and the steam is stopped from being supplied because an emergency situation occurs, and the like.

In an exemplary embodiment of the present application, the steam to be introduced into the reactor during the purge process may be fresh steam or wastewater distillation steam recycled from the product after the oxidative dehydrogenation reaction.

When the steam to be introduced into the reactor during the purge process is wastewater distillation steam recycled from the product after the oxidative dehydrogenation reaction, it is preferred to introduce the wastewater distillation steam into the reactor simultaneously with oxygen during the purge process.

It is preferred that the required amount of oxygen to be introduced simultaneously with the wastewater distillation steam is a calculated value or more in which carbon of hydrocarbons of the wastewater distillation steam may be completely oxidized into $CO_2$. When the amount of oxygen introduced is less than the required amount, the life of the catalyst is likely to be reduced.

In an exemplary embodiment of the present application, it is possible to maintain the same temperature as the temperature during the oxidative dehydrogenation reaction at the time of the purge process. By maintaining the temperature as described above, it is possible to reduce the energy and time cost consumption such as a temperature increasing process of a reactor during the restart of the oxidative dehydrogenation reaction and to quickly recover from the emergency situation to a normal operation state.

In an exemplary embodiment of the present application, during the restart of the oxidative dehydrogenation reaction after the purge process is completed, the oxygen may be introduced into the reactor before the butene, or the oxygen may be introduced into the reactor simultaneously with the butene, in the same manner as during the first start-up of the oxidative dehydrogenation reaction.

In an exemplary embodiment of the present application, the oxidative dehydrogenation reaction may be performed at a temperature of 250° C. to 500° C. Further, the oxidative dehydrogenation reaction may be performed at a reaction temperature of 250° C. to 500° C., 300° C. to 450° C., 320° C. to 400° C., 330° C. to 380° C., or 350° C. to 370° C. as an example, and within this range, the reaction efficiency is excellent without significantly increasing the energy costs, so that butadiene may be provided with high productivity.

In an exemplary embodiment of the present application, when the oxygen in the reactant comprising the butene, the oxygen, the nitrogen, and the steam is stopped from being supplied to the reactor, the method may comprise cooling the temperature of the reactor to 300° C. or less, may comprise cooling the temperature of the reactor to 20° C. to 300° C., and may comprise cooling the temperature of the reactor to 20° C. to 200° C. When the oxygen in the reactant comprising butene, oxygen, nitrogen, and the steam is stopped from being supplied, by cooling the temperature of the reactor to 300° C. or less or 200° C. or less, it is possible to stop the catalyst reaction, and accordingly, it is possible to prevent the activity of the catalyst from deteriorating.

In an exemplary embodiment of the present application, a molar ratio of butene:oxygen:nitrogen:steam may be 1:(0.1 to 1.5):(1 to 15):(0.5 to 10), and may be 1:(0.5 to 1.2):(5 to 12):(0.5 to 5).

In an exemplary embodiment of the present application, the reactor used in the oxidative dehydrogenation reaction is not particularly limited when the reactor is a reactor which may be used in the oxidative dehydrogenation reaction, but may be, as an example, a reactor in which the reaction temperature of a catalyst layer installed is maintained at a constant level and the oxidative dehydrogenation is performed while the reactant continuously passes through the catalyst layer. A specific example thereof may be a tube-type reactor, a batch-type reactor, a fluidized bed reactor, or a fixed bed reactor. The fixed bed reactor may be a multitube reactor or plate reactor as an example.

In an exemplary embodiment of the present application, the oxidative dehydrogenation reaction process may be performed using two reactors, in the form of a first reactor and a second reactor connected in series. In this case, the reactant comprising butene, oxygen, nitrogen, and steam may be introduced into the first reactor, a product passing through the first reactor may be introduced into the second reactor, and oxygen and/or air may be additionally introduced into the second reactor.

In an exemplary embodiment of the present application, the butene may comprise a C4 mixture. The C4 mixture comprises one or more normal butenes selected from 2-butene (trans-2-butene, cis-2-butene) and 1-butene as an example, and optionally, may further comprise normal butane or C4 raffinate-3.

In an exemplary embodiment of the present application, the steam or nitrogen ($N_2$) is a diluted gas introduced for the purpose of reducing the explosion danger of the reactant, preventing coking of the catalyst, removing the reaction heat, and the like, in the oxidative dehydrogenation reaction.

In an exemplary embodiment of the present application, the oxygen (02) is an oxidant and reacts with C4 fractions to cause a dehydrogenation reaction.

Hydrogen of butane or butene is removed by the oxidative dehydrogenation reaction, and as a result, butadiene is prepared. Meanwhile, the oxidative dehydrogenation reaction may produce a side reaction product comprising carbon monoxide (CO), carbon dioxide ($CO_2$), or the like, in addition to the main reaction such as Reaction Formula 1 or 2. The oxidative dehydrogenation reaction may comprise a process in which the side reaction product is separated so as not to be continuously accumulated in the process, and is released out of the system.

In an exemplary embodiment of the present application, the butene comprises a C4 mixture, the C4 mixture and the oxygen may be introduced into the first reactor at a molar ratio of 1:0.4 to 1.0, and at a molar ratio of 1:0.45 to 0.85. Further, in an exemplary embodiment of the present application, in addition to a first product passing through the first reactor, oxygen having a molar ratio of 0.1 to 0.45 based on 1 mole of the C4 mixture to be introduced into the first reactor may be additionally introduced into the second reactor, and oxygen having a molar ratio of 0.15 to 0.4 based on 1 mole of the C4 mixture to be introduced into the first reactor may be additionally introduced into the second reactor. A calorific amount during the reaction may be adjusted by introducing the C4 mixture, the oxygen, and the like at the molar ratio as described above. When the amount of oxygen is excessive as a case of being out of the molar ratio, the heat generation of the catalyst is high, so that the catalyst may be quickly deactivated, the selectivity for COx may be increased, and a possibility that a run-away phenomenon in the reactor may occur is increased. In addition, since the risk of explosion due to a possible flare in a factory complex is increased due to the increase in amount of unreacted oxygen, it is not appropriate for a commercial process to introduce oxygen in an excessive amount. Furthermore, when the amount of oxygen is insufficient, consumed oxygen in the catalyst is not replenished, so that the reactivity of the catalyst may be reduced, and the catalyst may be quickly deactivated.

In an exemplary embodiment of the present application, the first reactor and the second reactor may each independently comprise one or more of a bismuth-molybdenum-based catalyst and a ferrite-based catalyst.

The ferrite-based catalyst may be represented by the following Formula 1.

$$AFe_2O_4 \qquad \text{[Formula 1]}$$

In Formula 1, A is Cu, Ra, Ba, Sr, Ca, Cu, Be, Zn, Mg, Mn, Co, or Ni.

In an exemplary embodiment of the present application, it is preferred that the ferrite-based catalyst is a zinc ferrite catalyst.

The bismuth-molybdenum-based catalyst may be represented by the following Formula 2.

$$Mo_aBi_bC_cD_dE_eO_f \qquad \text{[Formula 2]}$$

In Formula 2,

C is one or more of trivalent cation metal components,

D is one or more of divalent cation metal components,

E is one or more of monovalent cation metal components, and when a is 12, b is 0.01 to 2, c is 0.001 to 2, d is 5 to 12, e is 0 to 1.5, and f is a value determined to match the valence by the other components.

The trivalent cation metal component may be one or more selected from the group consisting of Al, Ga, In, Ti, Fe, La, Cr, and Ce.

The divalent cation metal component may be one or more selected from the group consisting of Be, Mg, Ca, Sr, Ba, Ra, Co, Zn, and Cu.

The monovalent cation metal component may be one or more selected from the group consisting of Li, Na, K, Rb, Cs, Ag, and Fr.

According to an exemplary embodiment of the present application, in the method for preparing butadiene, the conversion of butene may be 72% or more, preferably 72.5% or more, and more preferably 79% or more.

According to an exemplary embodiment of the present application, in the method for producing butadiene, the selectivity of butadiene may be 85% or more, preferably 85.8% or more, and more preferably 87% or more.

According to an exemplary embodiment of the present application, the yield of butadiene may be 74% or more, preferably 74.4% or more.

Figure 1:
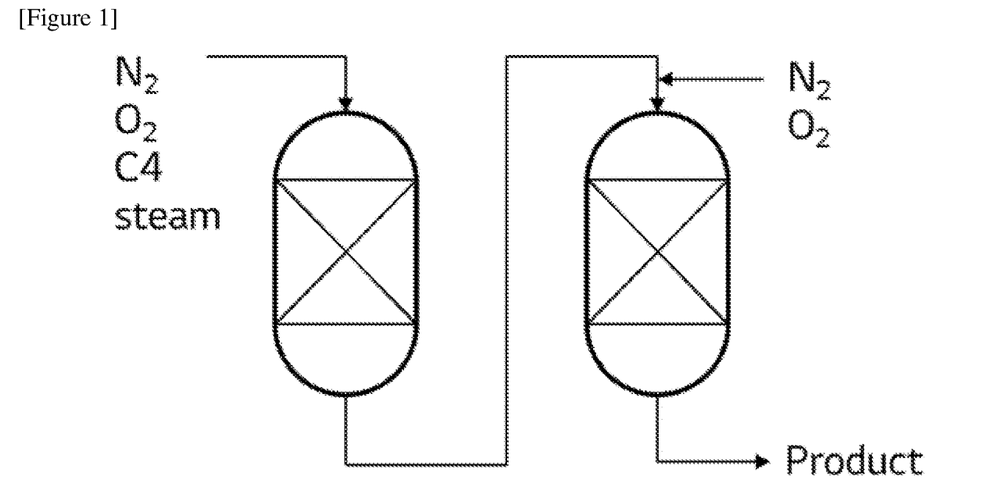
FIG. 1 is a process view of an oxidative dehydrogenation reaction according to an exemplary embodiment of the present application, and illustrates a process of a flow in which a reactant is introduced into the top of a first reactor and oxygen is divided and introduced into the top of a second reactor.
Figure 2:
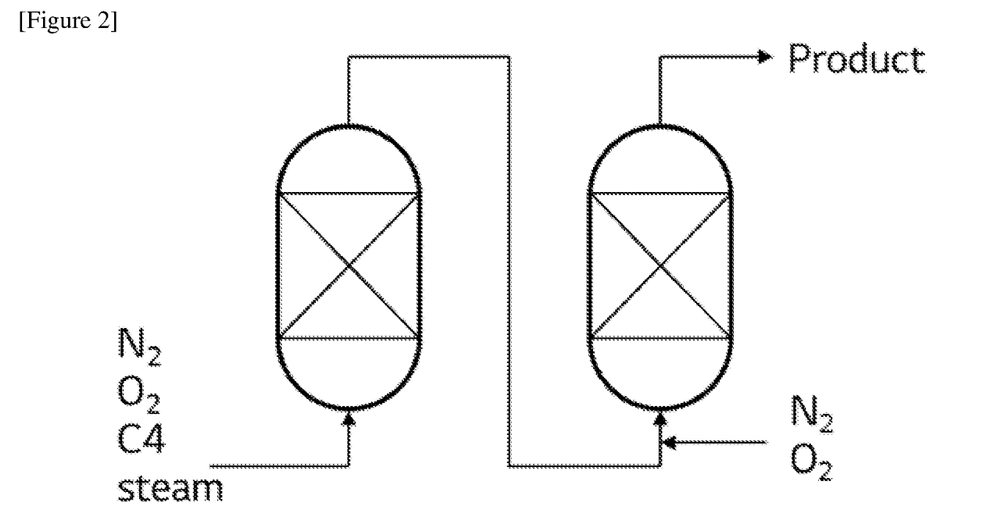
FIG. 2 is a process view of an oxidative dehydrogenation reaction according to an exemplary embodiment of the present application, and the process is a process of a flow in which a reactant is introduced into the bottom of a first reactor and oxygen is divided and introduced into the bottom of a second reactor.

A process view of an oxidative dehydrogenation reaction according to an exemplary embodiment of the present application is schematically illustrated in the following FIGS. 1 and 2. More specifically, the following FIG. 1 illustrates a process of a flow in which a reactant is introduced into the top of a first reactor and oxygen is divided and introduced into the top of a second reactor. Further, the following FIG. 2 illustrates a process of a flow in which a reactant is introduced into the bottom of a first reactor and oxygen is divided and introduced into the bottom of a second reactor.

According to an exemplary embodiment of the present application, during a first start-up of an oxidative dehydrogenation reaction, it is possible to prevent activity of a catalyst from deteriorating by introducing oxygen into a reactor before the butene or introducing oxygen into a reactor simultaneously with the butene.

Further, according to an exemplary embodiment of the present application, by performing a purge process while maintaining the same temperature as the temperature during an oxidative dehydrogenation reaction at the time of an emergency situation in which at least a part of a reactant comprising butene, oxygen, nitrogen, and steam is stopped from being supplied, it is possible to reduce the energy and time cost consumption such as a temperature increasing process of a reactor and to quickly recover the emergency situation to a normal operation state.

EXAMPLES

Hereinafter, the present application will be described in detail with reference to Examples for specifically describing the present application. However, the Examples according to the present application may be modified in various forms, and it is not interpreted that the scope of the present application is limited to the Examples described in detail below. The Examples of the present application are provided for more completely explaining the present application to the person with ordinary skill in the art.

EXAMPLES

<Preparation of Catalyst>

After a catalyst slurry was prepared by a method of mixing and co-immersing water in which $ZnCl_2$, $FeCl_3 \cdot 6H_2O$ was dissolved and water in which aqueous ammonia was dissolved, the catalyst slurry was filtered and residual ions were washed using a filter press, and a catalyst was synthesized on zinc ferrite by a method for drying and firing the filtered catalyst slurry. After the synthesized catalyst was ground, sieved, and then dispersed in water, the catalyst was coated by a wet method of mixing the dispersion with an alumina support in the form of a sphere, and evaporating water under reduced pressure.

<Oxidative Dehydrogenation Reaction>

1) Filling of Catalyst

For both a first reactor and a second reactor, a cylindrical shell and tube reactor having an inner diameter of 2.54 cm was used. After a mesh stand that could support a catalyst was placed at the bottom of the reactor, the reactor was filled with 50 cc of an alumina ball having a diameter of 3 mm, 1,000 cc of the catalyst in Preparation Example 1 thereon, and 350 cc of an alumina ball having a diameter of 3 mm again. The catalyst filling methods of the first reactor and the second reactor are the same as each other.

2) Dehydrogenation Reaction of Normal-Butene

As a reaction feed, a mixture of trans-2-butene and cis-2-butene was used. One or more of a C4 chemical such as 1-butene, isobutene, isobutylene, butane, and butadiene and a C5 chemical may be mixed with the reaction feed.

The reaction feed was introduced such that the space velocity for the catalyst was 250 $h^{-1}$ based on 1-butene or 2-butene. Oxygen was divided and introduced into the first reactor and the second reactor. Oxygen with a molar ratio of 0.47 based on 1 mole of initially introduced 2-butene was introduced into the first reactor, and oxygen with a molar ratio of 0.2 based on 1 mole of initially introduced 2-butene was introduced into the second reactor. Nitrogen with a molar ratio of 1.88 based on 1 mole of initially introduced 2-butene along with a reaction feed was introduced into the first reactor, and nitrogen with a molar ratio of 0.8 based on 1 mole of initially introduced 2-butene was introduced into the second reactor.

Steam with a molar ratio of 5 based on 1 mole of initially introduced 2-butene was introduced into the first reactor along with the reaction feed. Steam was mixed with the reaction feed in the front of the first reactor and introduced into the first reactor.

For both a first reactor and a second reactor, a shell and tube reactor having an inner diameter of 2.54 cm was used, and the temperature inside the reactor was adjusted by a method of heating heat-transfer salt filled in the external jacket of the reactor by an electric furnace. The first reactor salt temperature and the second reactor salt temperature were adjusted so as to be 350° C. and 370° C., respectively.

<Experimental Conditions>

1) Start-up (S/U): While the temperature was increased to the reaction temperature without a separate pre-treatment, nitrogen & oxygen (air), nitrogen, nitrogen & steam, or nitrogen & polluted steam (p. steam) were supplied, and when the temperature inside the catalyst filling layer reached 330° C., the other reactants were each supplied as in the order shown in the following table, and the reaction was started while maintaining the reaction temperature at 370° C.

2) Purge: Assuming an emergency situation, when a part of reactants of nitrogen, oxygen, steam (or polluted steam) and butene are stopped from being supplied, a purge process was performed under atmosphere shown in the following table while maintaining the reaction temperature at 370° C.

3) Restart: Since the reaction temperature was maintained at 370° C., the reaction was restarted by again supplying the reactants as in the order shown in the following table when the emergency situation was released.

4) Restart after shut-down (S/D): The reactor was also cooled to room temperature while performing the purge process under atmosphere shown in the following table, and then the reaction was started by again increasing the temperature as in the start order shown below.

Example 1

Air S/U and Restart: Nitrogen & Oxygen→Steam→Final supply of butene

Air purge: Air was supplied for 24 hours while maintaining the reaction temperature

TABLE 1

|  | Reaction condition | | | |
|---|---|---|---|---|
|  | S/U | STD #1 | STD(Δ) #2 | STD(Δ) |
| Butene conversion (%) | Air | 80.5 | Air purge 80.9(+0.4) | Air S/D restart 82.0(+1.1) |

TABLE 1-continued

|  | Reaction condition | | | |
|---|---|---|---|---|
|  | S/U | STD #1 | STD(Δ) #2 | STD(Δ) |
| Selectivity (%) of butadiene |  | 85.1 | 85.2(+0.1) | 85.5(+0.3) |

As in the result in Table 1, deterioration in activity of the catalyst caused by the air purge was not observed.

Comparative Example 1

$N_2$ S/U and Restart: Nitrogen→Steam→Butene→Final supply of oxygen $N_2$ purge: N2 was supplied and treated for 9 hours or 60 hours while maintaining the reaction temperature

TABLE 2

|  | Reaction condition | | | | | | | | |
|---|---|---|---|---|---|---|---|---|---|
|  | S/U | STD #1 | STD(Δ) #2 | STD(Δ) | STD(Δ) #3 | STD(Δ) | STD(Δ) #4 | STD(Δ) |
| Butene conversion (%) | $N_2$ | 76.2 | $N_2$ purge | 73.2 (−3.0) | $N_2$ restart | 72.5 (−0.7) | $N_2$ purge | 70.8 (−0.7) | $N_2$ purge 60 hr | 69.8 (−1.0) $N_2$ 9 hr |
| Selectivity (%) of butadiene |  | 83.8 |  | 82.1 (−1.7) |  | 82.1 (—) |  | 81.7 (−0.4) |  | 81.5 (−0.2) |

As in the result in Table 2, a continuous reduction in activity of the catalyst was observed depending on the repetition of $N_2$ purge.

Example 2

Steam S/U: The temperature of the reactor started to be increased in a nitrogen & steam atmosphere.

The reaction start conditions were set as in the following Table 3.

TABLE 3

| Reaction condition | Reaction start condition | | | | | |
|---|---|---|---|---|---|---|
|  | Nitrogen & Oxygen → Steam → Final supply of butene | | Nitrogen & Steam → Simultaneous supply of butene & oxygen | | Nitrogen & Polluted Steam → Simultaneous supply of butene & oxygen | |
|  | S/U | STD | S/U | STD(Δ) | S/U | STD(Δ) |
| Butene conversion (%) | Air | 80.5 | Fresh Steam | 80.7(+0.2) | P. Steam | 81.5(−0.5) |
| Selectivity (%) of butadiene |  | 85.1 |  | 85.6(+0.5) |  | 85.5(—) |

As in the results in Table 3, when oxygen was introduced before butene, or oxygen and butene were simultaneously introduced, the deterioration in activity of the catalyst was not observed. Further, when polluted steam is applied, the activity of the catalyst is likely to deteriorate even though oxygen and butene are simultaneously introduced, so that it is preferred to simultaneously introduce polluted steam and oxygen.

Comparative Example 2

Steam S/U: The temperature of the reactor started to be increased in a nitrogen & steam atmosphere.

The reaction start conditions were set as in the following Table 4.

TABLE 4

| | Reaction start condition | | | | | |
|---|---|---|---|---|---|---|
| | Nitrogen & Oxygen → Steam → Final supply of butene | | Nitrogen & Steam → Butene → Final supply of oxygen | | Nitrogen & Polluted Steam → Butene → Final supply of oxygen | |
| Reaction condition | S/U | STD | S/U | STD(Δ) | S/U | STD(Δ) |
| Butene conversion (%) | Air | 80.5 | Fresh Steam | 76.2(−4.3) | P. Steam | 74.0(−6.5) |
| Selectivity (%) of butadiene | | 85.1 | | 83.9(−1.2) | | 82.9(−2.2) |

As in the result in Table 4, when butene was supplied before oxygen, the deterioration in activity of the catalyst was observed.

Example 3

The purge process conditions were set as in the following Table 5.

TABLE 5

| | Reaction start condition | | | | | |
|---|---|---|---|---|---|---|
| | Nitrogen & Oxygen → Steam → Final supply of butene | | Nitrogen & Steam → Simultaneous supply of butene & oxygen | | Steam & Oxygen → Nitrogen → Butene → Adjustment of oxygen flow rate | |
| Reaction condition | S/U | STD(Δ) | S/U | STD(Δ) | S/U | STD(Δ) |
| Butene conversion (%) | Air purge | 80.9(+0.4) | Fresh Steam purge | 80.8(+0.1) | P. Steam + O₂(OBR = 0.01) purge | 81.9(+0.4) |
| Selectivity (%) of butadiene | | 85.2(+0.1) | | 85.5(−0.1) | | 85.3(−0.2) |

Comparative Example 3

The purge process conditions were set as in the following Table 6.

TABLE 6

| | Reaction start condition | | | | | |
|---|---|---|---|---|---|---|
| | Nitrogen & Steam → Butene → Final supply of oxygen | | Nitrogen & Polluted Steam → Butene → Final supply of oxygen | | Steam & Butene → Nitrogen → Final supply of oxygen | |
| Reaction condition | S/U | STD(Δ) | S/U | STD(Δ) | S/U | STD(Δ) |
| Butene conversion (%) | Fresh Steam purge | 72.4(−3.8) | P. Steam purge | 69.6(−4.4) | Butene + Steam Purge 9 hr | 67.6(−2.2) |
| Selectivity (%) of butadiene | | 82.5(−1.4) | | 81.3(−1.6) | | 80.7(−0.8) |

Example 4

As in the following Table 7, after the P. steam purge, air purge was continuously performed on the catalyst of which the activity deteriorated.

TABLE 7

| | Reaction start condition | | | | | | |
|---|---|---|---|---|---|---|---|
| | Nitrogen & Oxygen → Steam → Final supply of butene | Nitrogen & Steam → Simultaneous supply of butene & oxygen | | Nitrogen & Oxygen → Steam → Final supply of butene | | Nitrogen & Oxygen → Steam → Final supply of butene | |
| Reaction condition | STD | S/U | STD(Δ) | S/U | STD(Δ) | S/U | STD(Δ) |
| Butene conversion (%) | 81.9 | P. Steam Purge 9 hr | 77.4 (−4.5) 84.1 (−1.2) | Air Purge (370° C.) 9 hr | 78.4 (+1.0) 84.1 (—) | Air Purge (400° C.) 9 hr | 79.3 (+0.9) 84.8 (+0.7) |
| Selectivity (%) of butadiene | 85.3 | | | | | | |

As in the results, according to an exemplary embodiment of the present application, during a first start-up of an oxidative dehydrogenation reaction, it is possible to prevent activity of a catalyst from deteriorating by introducing oxygen into a reactor before the butene, or introducing oxygen into a reactor simultaneously with the butene.

Further, according to an exemplary embodiment of the present application, by performing a purge process while maintaining the same temperature as the temperature during an oxidative dehydrogenation reaction at the time of an emergency situation in which at least a part of a reactant comprising butene, oxygen, nitrogen, and steam is stopped from being supplied, it is possible to reduce the energy and time cost consumption such as a temperature increasing process of a reactor and to quickly recover the emergency situation to a normal operation state.

In addition, according to an exemplary embodiment of the present application, at the time of an emergency situation in which at least a part of a reactant comprising butene, oxygen, nitrogen, and steam is inadvertently stopped from being supplied, the constitution of the reactant which continues to be supplied may be a basis for determining whether the activity of a catalyst deteriorates depending on the constitution of the reactant which continues to be supplied. Accordingly, it is possible to reduce the energy and time cost consumption by enabling the re-operation or catalyst replacement to be determined.

The invention claimed is:

1. A method for producing butadiene, the method comprising performing an oxidative dehydrogenation reaction step by introducing a reactant comprising butene, oxygen, nitrogen, and steam into a reactor which is filled with a catalyst,
   wherein during a first start-up of the oxidative dehydrogenation reaction:
   (1) oxygen and nitrogen are first simultaneously introduced into the reactor, and then steam is introduced into the reactor, and then butene is finally introduced into the reactor; or
   (2) nitrogen and steam are first simultaneously introduced into the reactor, then oxygen and butene are simultaneously introduced into the reactor; or
   (3) steam and oxygen are first simultaneously introduced into the reactor, then nitrogen is introduced into the reactor, and then butene is finally introduced into the reactor;
   wherein when at least a part of the reactant comprising butene, oxygen, nitrogen, and steam is stopped from being supplied, the oxidative dehydrogenation reaction is stopped and a purge process is performed by introducing one or more of air and steam into the reactor where the temperature during the oxidative dehydrogenation reaction is maintained at the time of the purge process.

2. The method of claim 1, wherein the steam is wastewater distillation steam recycled from a product obtained from the oxidative dehydrogenation reaction, and
   the wastewater distillation steam is introduced into the reactor simultaneously with oxygen in step (3) during the first start-up.

3. The method of claim 1, wherein the steam to be introduced into the reactor during the purge process is wastewater distillation steam recycled from a product obtained from the oxidative dehydrogenation reaction, and
   the wastewater distillation steam is introduced into the reactor simultaneously with oxygen during the purge process.

4. The method of claim 1, wherein during a restart of the oxidative dehydrogenation reaction after the purge process is completed, the reactant comprising butene, oxygen, nitrogen, and steam is introduced into the reactor in the same manner as during the first start-up.

5. The method of claim 1, wherein the oxidative dehydrogenation reaction is performed at a temperature of 250° C. to 500° C., and
   when the oxygen in the reactant comprising the butene, the oxygen, the nitrogen, and the steam is stopped from being supplied to the reactor, the method comprises cooling the temperature of the reactor to 300° C. or less prior to the purge process.

6. The method of claim 1, wherein the oxidative dehydrogenation reaction process is performed using two reactors including a first reactor and a second reactor connected in series, and
   the reactant comprising butene, oxygen, nitrogen, and steam is introduced into the first reactor.

7. The method of claim 6, wherein the butene comprises a C4 mixture, and the C4 mixture and oxygen are introduced into the first reactor at a molar ratio of the C4 mixture:oxygen of 1:0.4 to 1.0.

8. The method of claim 7, wherein oxygen with a molar ratio of 0.1 to 0.45 based on 1 mole of the C4 mixture to be introduced into the first reactor is further introduced into the second reactor.

9. The method of claim 6, wherein the first reactor and the second reactor each independently comprise one or more of a bismuth-molybdenum-based catalyst and a ferrite-based catalyst.

10. The method of claim 9, wherein the ferrite-based catalyst is represented by the following Formula 1:

[Formula 1]

$AFe_2O_4$ in Formula 1, A is Cu, Ra, Ba, Sr, Ca, Cu, Be, Zn, Mg, Mn, Co, or Ni.

11. The method of claim 9, wherein the bismuth-molybdenum-based catalyst is represented by the following Formula 2:

[Formula 2]

$Mo_aBi_bC_cD_dE_eO_f$ in Formula 2,

C is one or more of trivalent cation metal components,

D is one or more of divalent cation metal components,

E is one or more of monovalent cation metal components, and when a is 12, b is 0.01 to 2, c is 0.001 to 2, d is 5 to 12, e is 0 to 1.5, and f is a value determined to match the valence by the other components.

\* \* \* \* \*